United States Patent [19]

Behney

[11] 4,147,164
[45] Apr. 3, 1979

[54] METHOD OF PERFORMING IMPLANTATIONS IN A CANINE EAR OR THE LIKE FOR CORRECTIONAL PURPOSES

[76] Inventor: Charles A. Behney, Box 4137, Bisbee, Ariz. 85603

[21] Appl. No.: 768,101

[22] Filed: Feb. 14, 1977

[51] Int. Cl.² ............................ A61D 1/00; A61F 1/24
[52] U.S. Cl. ................................ 128/76 R; 128/330;
128/347; 128/2 B; 3/1; 3/1.9; 119/96
[58] Field of Search ............. 128/2 B, 305, 217, 221,
128/264, 133, 76 R, 82, 83, 347, 330, 316, 329 R, 348, 350 R, 215; 3/1; 119/96, 143

[56] References Cited

U.S. PATENT DOCUMENTS

| | | | |
|---|---|---|---|
| 1,655,158 | 1/1928 | Muir | 128/217 |
| 2,219,605 | 10/1940 | Turkel | 128/221 |
| 2,922,420 | 1/1960 | Cheng | 128/221 |
| 3,007,471 | 11/1961 | McClure | 128/305 |
| 3,620,216 | 11/1971 | Szymanski | 128/217 |
| 3,788,320 | 1/1974 | Dye | 128/221 |
| 3,820,545 | 6/1974 | Jefferts | 128/217 |
| 3,921,632 | 11/1975 | Bardini | 128/264 |
| 3,994,287 | 11/1976 | Turp et al. | 128/347 |
| 4,010,494 | 3/1977 | Sauer | 119/96 |

FOREIGN PATENT DOCUMENTS 156651  4/1962  U.S.S.R. .................................. 128/305

Primary Examiner—Robert W. Michell
Assistant Examiner—Arthur S. Rose
Attorney, Agent, or Firm—Norman H. Gerlach

[57] ABSTRACT

A method of performing canine ear or other implantations in order to correct a faulty ear carriage by erection of the ear, utilizing three basic surgical pieces or implements in the form of (1) an elongated cut-forming shank (trocar) having a sharp distal end which is used to incise the ear so that the shank may be pushed along the general plane of the ear between the outer skin and the inner cartilage to create a duct which crosses over or bridges the weakened area of the cartilage, (2) an open-ended sheath (cannula) which is slidable onto the shank in close fitting relation and is adapted to be pushed into the duct as it is being created by the shank to the end that when the shank is withdrawn from the thus inserted sheath the latter remains within the duct and establishes an open-ended tunnel for reception of an ear-rigidifying implant, and (3) a pusher or thrust member which has a blunt forward end and is used to push the implant into the tunnel and consequently into the duct, and to hold it there while the sheath is being withdrawn. Withdrawal of the sheath from the duct by sliding it rearwardly on the thrust member, followed by withdrawal of the thrust member, leaves the implant embedded in the duct which then collapses or shrinks on the implant. A minor suture closes the initial incision at the mouth of the duct and the implantation is thus completed in an exceptionally short length of time and with a minimum amount of pain and hemorrhage.

11 Claims, 21 Drawing Figures

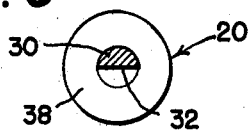
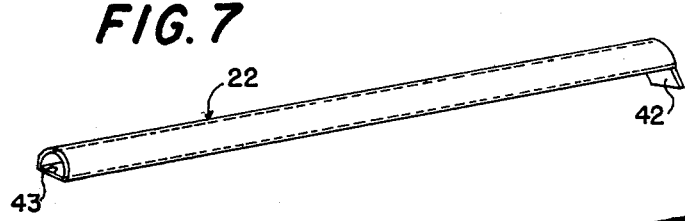
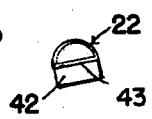
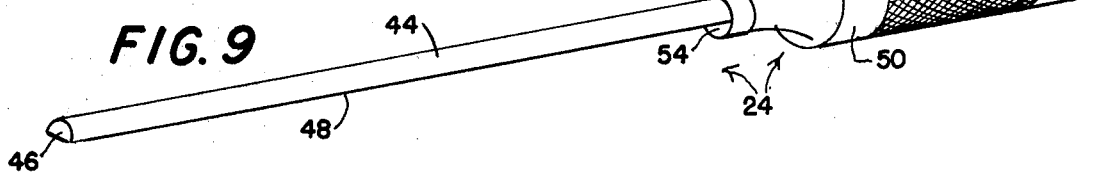
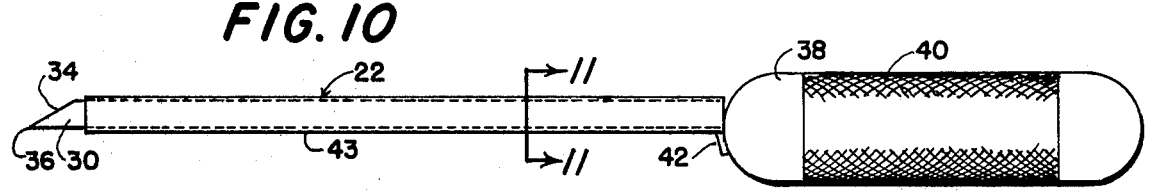
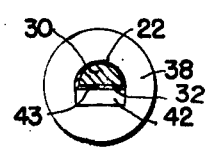
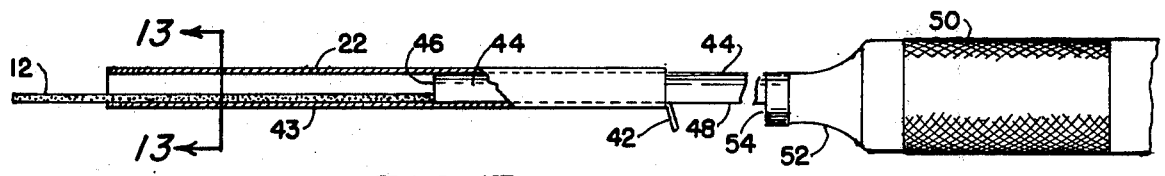
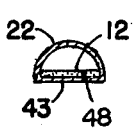
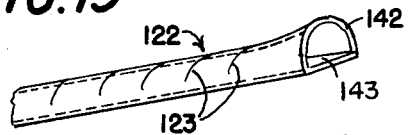
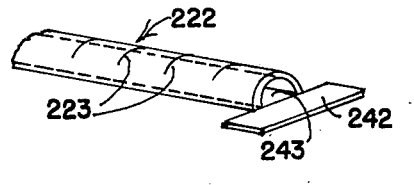
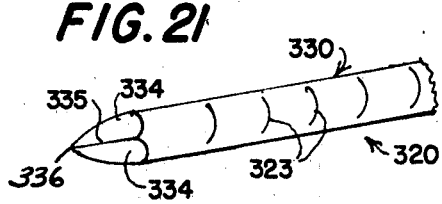

METHOD OF PERFORMING IMPLANTATIONS IN A CANINE EAR OR THE LIKE FOR CORRECTIONAL PURPOSES

The present invention relates generally to a surgical procedure and has particular reference to a method of performing a canine ear implantation or the like in order to correct a faulty ear carriage and thus cause the ear to stand erect or upright.

Heretofore various procedures have been employed in veterinary practice in order to correct a faulty ear carriage in dogs, the earliest procedure being based upon simple scarification so as to increase the rigidity of the auricular cartilage. While some scarification procedures have proven successful, in a large number of instances either the scar tissue lacks sufficient rigidity to afford proper ear support or rigidity, or excess fibrous tissue develops and results in a cosmetically unacceptable thickening of the ear. More recently, homologous cartilage grafts have been employed with a fair measure of success, but such grafts require a collection of proper cartilage or other material from other medically compatible animals, or the same animal, the storing thereof, and the performance of relatively complicated surgical steps in order to effect the desired transplantation.

Still more recently, veterinary surgeons have experimented with the use of non-homologous reinforcing ear implants such as wood, whale bone, and various plastics such as Celluloid, Nylon, Teflon, polypropyline and the like. The use of such materials presents or is accompanied by at least two important difficulties. Unless the material possesses biocompatibility, excessive tissue response frequently leads to distortion of the ear or extrusion of the implant after a period of time. Sometimes, even when the material does possess the necessary compatibility, it will produce only minimal tissue bonding reaction and this results in instability of the implant due to lack of tissue encapsulation with consequent implant extrusion as in the case of incompatible implants. A relatively recent evaluation of the use of synthetic implants has brought to light the use of porous high-density polyethylene implants. Such material has demonstrated excellent biocompatibility and its porous structure provides for rapid tissue ingrowth into the pores, thus resulting in firm fixation of the implant in the bed which is prepared for its reception. Because of the above outlined advantages of porous polyethylene implants, the present surgical procedure contemplates its use although it is not necessarily limited thereto.

Veterinarian practice currently in use with any of the known implants, including the aforementioned high-density porous polyethylene material, is relatively complicated and time-consuming and the period of convalescence which is involved after an ear implantation has been made is relatively long. Briefly, the current procedure is to make an incision along the longitudinal axis of the ear to be treated and slightly in excess of the length of the implant. The incision, of course, bridges or crosses over the weakened area of the ear cartilage and extends substantially at a right angle thereto. The incision usually extends along a major portion of the length of the ear. After the incision is made, the edges of the skin around the incision are spread apart so as to expose the bed on which the implant is to be laid and, at this time, the implant is cut to size and shape so that it fits the bed. Great care must be exercised in making the incision and in handling the skin flaps which it produces since perforation of the overlying skin would endanger the implantation. Furthermore, the length of the incision must be appreciably longer than that of the implant in order that when the surrounding skin edges are spread apart, ample exposure of the bed (cartilage) will occur since the rough porous surface of the implant precludes sliding of the implant on the cartilage for centering purposes. In some cases, especially where the weakened or faulty area to be corrected is near the base of the ear, it may be necessary to place the implant on the convex side of the cartilage and to anchor it at its ends with absorbable sutures in the muscles of the ear base. After the implant has been shaped and placed in centered relation on the cartilage bed, the skin is closed over the implant and sutured along the entire length of the original incision. From the above description, it will be clearly manifest or obvious that the number of involved heretofore mentioned surgical steps, each of which must be accompanied by approved antisepsis, such, for example, as rinsing the implant in a sterile solution, avoiding contact of the implant with the surface of the skin so that particles of hair will not adhere to it, the copius use of antibacterial prophylactics and antibiotics, etc., is extremely time-consuming and, therefore, expensive from a medical point of view. When such an implantation operation is successfully performed, the implant may become stabilized within two weeks so that the bandages and sutures may be removed. After a further period of time, the evidence of the operation disappears and the implant remains a permanent one with sufficient rigidity to maintain the ear erect but with enough flexibility to render a natural feel to the touch, as well as to the animal.

The present invention is designed to obviate the relatively large number of surgical steps that have heretofore been employed in connection with effecting of synthetic canine ear implantations and to produce a procedure which not only is less likely to enter complications during the involved surgery, but also effectively eliminates aftermath complications inasmuch as far fewer external sutures are required with no internal absorbable sutures whatsoever being involved. Furthermore, according to the present invention, the cartilage bed per se becomes, at no time, exposed to the gloves of the veterinary surgeon.

In carrying out the improved surgical procedure constituting a part of the present invention, three surgical pieces or implements are required, and these include a narrow elongated duct-forming shank which has a sharp distal end for creating an initial small incision near the outer end of the ear to be corrected by way of the implantation, and is fitted with a tubular, open-ended sheath which is slidable on the shank so that after the small incision is made and the shank has been pushed forwardly between the cartilage and the outer skin of the ear on either the convex or the concave side of the ear, the shank and its associated sheath establish a relatively deep pocket-like duct in a longitudinal direction within the ear, such duct traversing the weakened area of the cartilage. After formation of the duct, the shank is withdrawn from the sheath, thus leaving the latter embedded in the duct so that it establishes a tunnel which leads into the duct and into which the pre-cut implant may be inserted lengthwise. The third implement is in the form of an elongated pusher or thrust member which, after withdrawal of the incision-making shank while the sheath remains in the previously formed duct is used to push the implant endwise into the tunnel until the forward end of the implant engages the bottom or closed end of the pocket-like duct and then to hold the implant while the sheath is slid to a small extent rearwardly on the thrust member in order partly or fully to disengage it from the duct-embedded implant. At the conclusion of the last mentioned step, the walls of the duct, i.e., the skin and the cartilage, shrink or collapse upon the implant and the forward end region of the thrust member so that final withdrawal of the thrust member from the duct leaves these walls collapsed upon the implant. The small incision is then closed by one or two sutures or in any other suitable manner, and the operation is complete except for the antisepsis and surgical dressing procedures which are always employed in connection with any operation. With the above briefly outlined surgical procedure and the use of the associated implements, a relatively short period of convalescense is required before the dressing and sutures may be removed.

The provision of a surgical procedure for effecting canine ear or other implantations such as has briefly been outlined above, possessing the stated advantages, and utilizing the three aforementioned particular surgical implements, constitutes the principal object of the present invention. Numerous other objects and advantages of the invention, not at this time enumerated, will readily suggest themselves as the nature of the invention is better understood from a consideration of the following detailed description.

The invention consists in the several novel features which are hereinafter set forth and are more particularly described by the claims at the conclusion hereof.

In the accompanying three sheets of drawings forming a part of this specification, the invention is illustrated in detail.

In these drawings:

FIG. 6 is a transverse sectional view taken on the line 6—6 of FIG. 5;

FIG. 7 is a perspective view of a cannula-like sheath which is used in association with the implement of FIG. 4 and the implement of FIG. 5 in practicing the present invention;

FIG. 8 is a rear end view of the sheath of FIG. 7;

FIG. 9 is a front perspective view of a pusher or thrust implement which is used in association with the cannula-like sheath of FIG. 7 in practicing the present invention;

FIG. 10 is a side elevational view of the tissue-penetrating implement of FIG. 5 and its associated sheath of FIG. 7, showing the latter fully assembled upon the former preparatory to the assembly being used to make an incision as the preliminary step of the method of the present invention;

FIG. 11 is a transverse sectional view taken on the line 11—11 of FIG. 10;

FIG. 12 is a fragmentary side elevational view, partly in longitudinal section, illustrating the manner in which the thrust implement of FIG. 9 and the sheath of FIG. 7 are employed in association with each other in inserting the implant of FIG. 4 into the tunnel-like duct which is formed by way of the implement of FIG. 5;

FIG. 13 is a transverse sectional view taken on the line 13—13 of FIG. 12;

FIG. 19 is a fragmentary perspective view showing a modified form of a cannula-like sheath capable of use in performing the method of the present invention;

FIG. 20 is a fragmentary perspective view similar to FIG. 19 but showing a further modified form of sheath; and FIG. 21 is a fragmentary perspective view of a modified form of trocar-like tissue-penetrating implement for use in performing the present method.

Figure 1:
FIG. 1 is a fragmentary front view of a dog having faulty ear carriage in both ears and of a nature capable of being corrected by means of the implant method constituting the present invention.
Figure 2:
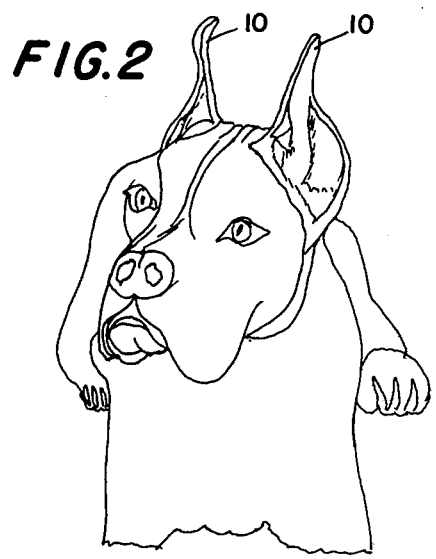
FIG. 2 is a fragmentary front view similar to FIG. 1 but showing the dog after the faulty ear carriage (both ears) has been corrected.
Figure 3:
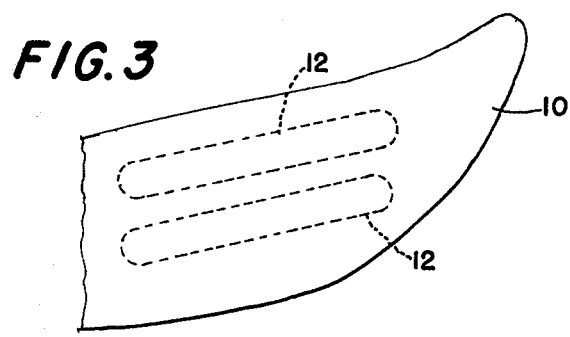
FIG. 3 is an enlarged fragmentary plan view of the inner or concave side of a fully healed canine ear, showing the position of the two corrective implants after being inserted into the ear by way of the present method.

Referring now to the drawings in detail and in particular to FIGS. 1 and 2, the former view is illustrative of a dog (boxer) having ears 10 which are faulty in that they do not stand erect but instead droop inwardly as shown. According to the surgical method of the present invention and by the use of three surgical implements which will be described in detail presently, this faulty ear condition may be permanently corrected so that such ears assume the erect condition illustrated in FIG. 2. Briefly, and with particular reference to FIG. 3 of the drawings, such faulty condition is remedied according to the present invention by the performance of a novel surgical technique or method of inserting one or more supportive implants within the ear in such a manner as to increase the rigidity of the auricular cartilage, two such implants being illustrated in FIG. 3 and designated by the reference numeral 12.

Conventional surgical implant operations are invariably carried out by making an incision, usually on the concave side of the auricular cartilage, the incision being of an elongated nature and extending at right angles to and crossing over the weakened area of the cartilage. The edges of the ear skin which extend around or define the incision are then spread apart in order to create a bed within which the implant may be placed, the implant, of course, being carefully cut to size as a preliminary to being placed on the bed. Thereafter, the skin folds are drawn over the implant and the skin edges of the incision sutured together to complete the procedure. According to the present invention, by the use of a three-piece surgical apparatus, an equally effective implant operation may be carried out, such operation producing substantially the same result but with considerably greater ease, consuming much less time, and involving less surgical complications including those that arise strictly from surgical procedure and those that are of an auxiliary nature such as microbial contamination and the like.

Figure 14:
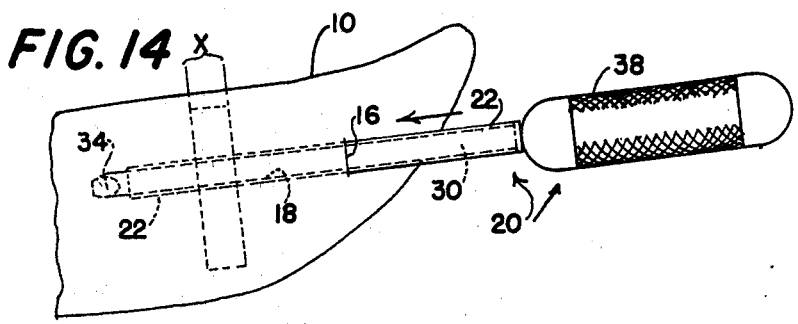
FIG. 14 is a plan view of a canine ear illustrating schematically the creation of an incision and longitudinal duct therein by means of the assembled tissue-penetrating implement of FIG. 5 and the associated sheath of FIG. 7.

Briefly, the surgical procedure or method which constitutes a principal part of the present invention involves the creation of an extremely short transverse incision such as that indicated at 16 in FIG. 14 at an appropriate point near the distal end of the canine ear 10, then causing a relatively deep or long narrow pocket-like duct 18 to extend immediately beneath the outer skin and between the skin and the adjacent cartilage and in such a manner that it extends over and across the weakened portion of the ear cartilage, then inserting a pre-cut or shaped implant, such as the implant 12, endwise through the incision 16 and into the duct 18 so that it lies wholly within the confines of the latter and substantially fills the same, and finally suturing the incision so as to capture the implant within the duct-containing body of the ear in reinforcing relationship with respect to the cartilage, thereby remedying the original deformation or faulty condition of the ear.

The above basic surgical procedure or method is made practical by the use of certain surgical implements, the nature of which will be set forth in detail presently, and by employing a specific technique involving a series of method steps which also will be specifically described in detail and subsequently claimed. These surgical implements are clearly illustrated in FIGS. 5 to 12, inclusive. They are three in number and consist of an incision-making and duct-forming tool 20 the details of which are best shown in FIGS. 5 and 6, a sheath 22 the details of which are best shown in FIGS. 7 and 8, and a thrust member 24 the nature of which is shown in FIG. 9.

The incision-making and duct-forming tool 20 and the sheath 22 are used according to the present invention in combination with each other substantially in the same manner that a surgical trocar and cannula combination is employed in establishing a drainage duct for body fluids, the procedure being to telescope the cannula over the trocar, insert the thus assembled assembly or combination into an existing body cavity and then withdraw the trocar from the inserted cannula so as to leave the cannula within the duct in order that it may serve as a drainage canal for body fluids for whatever time is necessary, after which the cannula may be removed and the duct allowed to resume its normal size or to close altogether, depending upon the particular nature of the duct. In some instances, the trocar is provided with a sharp point which pierces the skin so that the trocar and cannula combination establishes the drainage duct, while in other instances the trocar merely blocks the egress of material which otherwise would clog the cannula in the absence of the trocar. Due to the general similarity between the use of the incision-making and duct-forming tool 20 and its associated sheath 22 and the use of a surgical trocar and cannula combination in normal medical practice, the implement or tool 20 will hereinafter be referred to as a trocar, while the sheath 22 will be referred to hereafter as a cannula, such terminology also being considered as appropriate in the appended claims.

Figure 5:
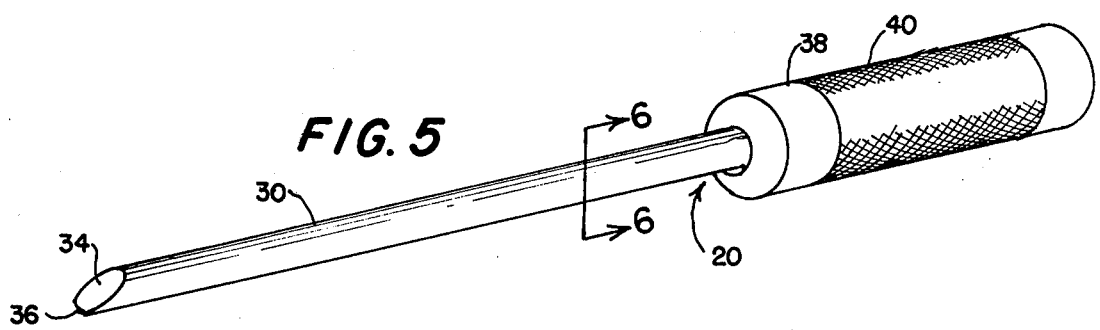
FIG. 5 is a front perspective view of a trocar-like tissue-penetrating implement which is employed, in combination with other implements, in practicing the implant method of the present invention.

Referring now particularly to FIGS. 5 and 6 of the drawings, the aforementioned duct-forming tool or trocar 20 embodies an elongated ear-penetrating shank 30 which is semi-circular in cross section, thus establishing a flat side 32 (see FIGS. 6 and 11) and a rounded or arcuate opposite side. Preferably, the shank 30 is formed of stainless steel for sanitary and other reasons. The forward or distal end of said shank is formed with an approximately 45° bevel 34 which establishes a short transverse slightly curved or arcuate cutting edge 36. The rear or proximate end of the shank 30 of the trocar 20 carries a suitable manipulating handle 38 which preferably is provided with a knurled section 40 which facilitates ease and accuracy of manipulation of the trocar as a whole.

The sheath or cannula 22 is in the form of an elongated tubular open-ended member which, like the shank 30 of the trocar 20, is preferably formed of stainless steel. It has a shape characteristic which is conformable to that of the shank 30 in that it is capable of fitting in sheath-like fashion over the shank in relatively close-fitting relationship as shown in FIG. 10 but which, nevertheless, is freely slidable on the shank. The length or longitudinal extent of the cannula 22 is slightly less than that of the shank 30 so that at least the bevelled surface 34 and the arcuate cutting edge 36 of the shank remains exposed when the cannula is fully fitted upon the shank as shown in FIG. 10. The proximate end of the cannula 22 is provided with an outwardly extending tab or ear 42 which serves as a handle or finger grip to facilitate insertion of the cannula over the shank of the trocar and removal of the trocar from the cannula to the end that it is unnecessary for the fingers of the surgeon to touch the main body of the cannula. A flat side wall 43 (see FIGS. 7, 8 and 11) on the cannula 22 underlies the flat side 32 of the trocar when the two parts are assembled.

The aforementioned thrust member 24 is shown in detail in FIG. 9 of the drawings and it embodies an elongated shank portion 44 the cross-sectional shape and size of which are precisely the same as the cross-sectional shape and size of the shank 30 of the trocar 20. However, the length of the shank portion 44 of the thrust member 24 is appreciably longer than that of the trocar shank 30 and also that of the cannula 22. The distal end 46 of the shank portion 44 of the thrust member 24 is of semi-circular configuration and extends at right angles to the longitudinal axis of the shank portion 44. Said shank portion, being semi-circular in cross section, is thus provided with a flat or planar side 48 as shown in FIG. 9. The thrust member 24 is preferably of one-piece stainless steel construction and the proximate end of the shank portion 44 is provided with a generally cylindrical handle 50, the forward end of which is of reduced diameter as indicated at 52 in order to provide a finger grip which facilitates manual longitudinal motivation of the member 24. The forward end of the handle 50 is provided with a semi-circular end face 54 which extends at right angles to the longitudinal axis of the thrust member and presents a juncture line with the flat side 48 of the shank portion 44, such end face constituting an abutment or shoulder for the out-turned tab or ear 42 on the cannula 22 to limit the extent of rearward sliding movement of the latter relatively to the thrust member 24 when the thrust member and cannula are assembled upon each other as shown in FIG. 12 of the drawings.

Figure 4:
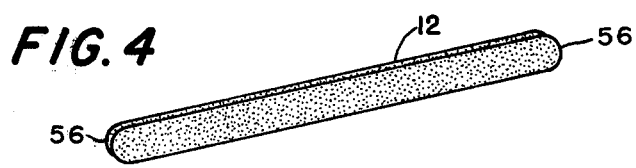
FIG. 4 is a perspective view of a typical implant.

Referring now to FIG. 4 of the drawings, the implant 12 which is shown in this view is of a non-homologous synthetic nature so far as ear cartilage is concerned and it may be formed of wood, whale bone, Celluloid, stainless steel, Nylon or any one of a number of synthetic materials which have heretofore been used as ear implants. Preferably, however, it is formed of polyethylene and, specifically of a substance known as "Biopar" (trade name) which is manufactured and sold by Glasrock Plastics Group of Fairburn, Ga. Although "Biopar" may have other medical uses, it is specifically sold in sheet form and is adapted to be cut into individual canine ear implants for the support of weak or defective auricular cartilage in dogs, that is, canine ears which fail to stand erect. "Biopar" is a special non-reactive, high-density, porous polyethylene substance having excellent biocompatibility and the porous nature of which allows animal tissue to grow into the pores and lock the implant in place. Stated otherwise, "Biopar" serves as a lattice work with numerous tiny voids that become filled with living tissue, thus locking the implant in place to form a synthesis which, although pliable, affords better support than either the "Biopar" or the cartilage alone. The positive fixation of the implant which is achieved by such tissue growth into the pores also minimizes the possibility of extrusion which frequently occurs when non-porous materials are used. "Biopar" comes in sterile sheet form and it is to be understood that the implants 12 are cut to the desired size and shape by the veterinary surgeon or the latter's assistant. The particular implant 12 which is illustrated herein (see FIG. 4) is of narrow elongated design with rounded ends 56, its width being slightly less than the width of the flat side wall 43 of the cannula so that it may be passed endwise through the latter during the surgical procedure as will be set forth presently.

The surgical procedure or method which is involved in connection with the use of the three aforementioned surgical implements, namely, the trocar 20, the cannula 22, and the thrust member 24 is sequentially and somewhat schematically illustrated in FIGS. 14 through 18 of the drawings, and in specifically describing such procedure, it will be understood that throughout the entire implant operation, the usual surgical antiseptic precautions and other steps for preventing hemorrhage and other unwanted complications are resorted to, these including the wearing of surgical gloves, an initial shaving of hair from the canine ear to be corrected by way of the "Biopar" implant 12, sterilization of the implements, and steps too numerous to mention.

Referring now to FIG. 14 of the drawings, after the ear 10 has been properly prepared for surgery, the cannula 22 is slipped over the shank 30 of the duct-forming tool or trocar 20 until the bevel 34 is exposed at the distal end of the cannula, after which the combination of trocar 20 and cannula 22 is used basically as a unit to form or make the transverse incision 16 and to drive the cannula 22 between the outer skin of the ear and the adjacent interiorly disposed cartilage in order to establish the elongated, longitudinally extending tunnel or duct 18 which crosses over the weakened area "x" (see FIG. 14) of the cartilage. Engagement of the forward end of the handle 38 of the trocar 20 with the proximate or rear end of the cannula 22 applies the necessary thrust to force the cannula into the ear and create the aforementioned duct 18.

Figure 15:
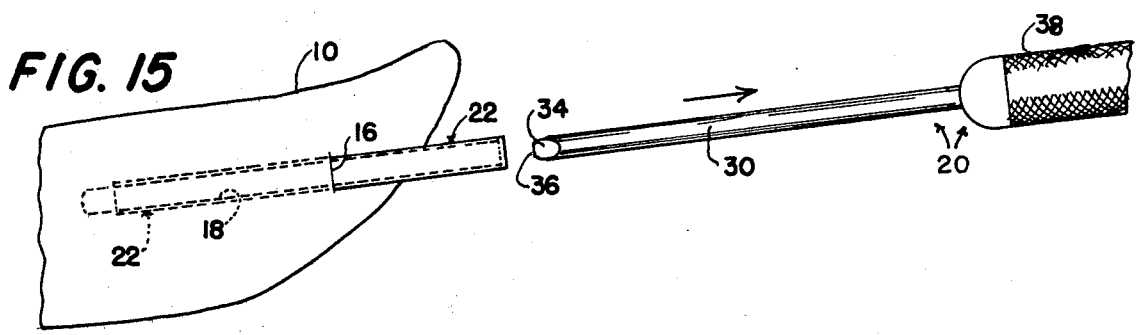
FIG. 15 is a plan view similar to FIG. 14 but showing the tissue-penetrating implement withdrawn from the sheath after it, with the assembled sheath thereon, has been used to form the incision and the longitudinal duct in the dog's ear.

Immediately after the duct 18 has thus been established, the trocar 20 is completely withdrawn from the cannula 22 as shown in FIG. 15, thereby leaving the cannula in the proper operative position, i,e., with its forward end region embedded or lodged in the trocar-formed duct 18 in the ear. In its operative position, the inner embedded end region of the cannula 22 serves to retain the duct 18 in a spread-apart condition, so to speak, so that the preformed or shaped implant 12 may subsequently be introduced into the duct through the cannula without tissue or cartilage interference. It is to be noted at this point that although it might be possible to insert the implant endwise into the duct by forcing it into position without the use of the cannula 22, such a procedure would be highly unsatisfactory due to the fact that the cartilage is possessed of a number of transverse and other ridges that would ordinarily resist insertion of the implant, damage the implant or the cartilage, or both, and would present frictional resistance which might engender or bring about improper alignment of the implant 12 with the duct 18 and otherwise occasion difficult implement manipulation. The flat smooth surface of the side wall 43 (see FIGS. 7 and 12) of the cannula 22 passes readily over these cartilage ridges, especially if an upward lift is applied to the handle 38 of the trocar 20 during insertion of the trocar-cannula combination into the ear 10 to form the duct 18.

Figure 16:
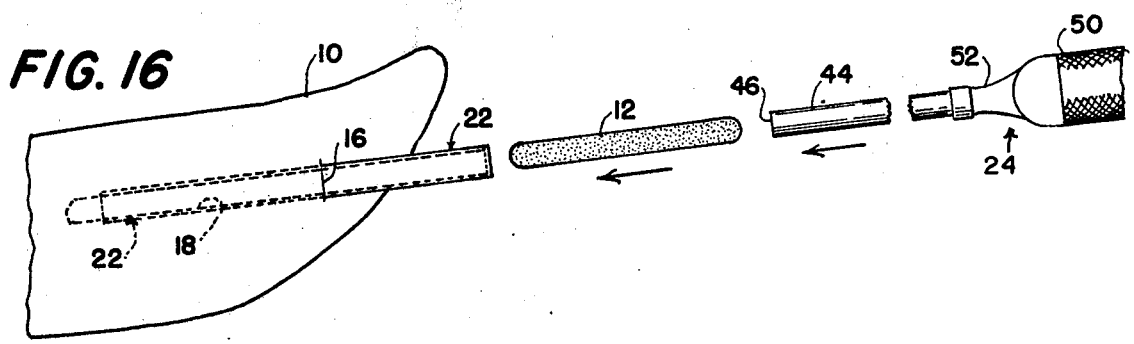
FIG. 16 is a plan view similar to FIG. 15 but illustrating schematically and in exploded fashion the manner in which an implant is projected into the cannula-like sheath for subsequent insertion into the duct which was previously formed in the ear by the assembly of tissue-penetrating implement and sheath.
Figure 17:
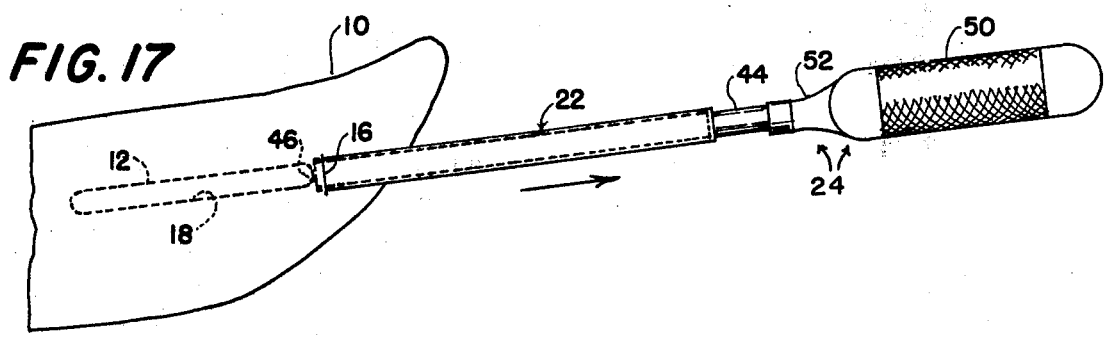
FIG. 17 is a plan view similar to FIG. 16 but showing the implant fully projected into the duct by way of the thrust implement of FIG. 9 and also the sheath after partial removal from the duct.

After the trocar 20 has been completely withdrawn from the cannula 22 as hereinbefore described and as shown in FIG. 15, the interior of the cannula presents a relatively wide tunnel into which the implant 12 may be inserted endwise and pushed into position by means of the thrust member 24 as illustrated in the exploded arrangement of FIG. 16. The blunt end 46 of the shank portion 44 of the member 24 is used to force the implant endwise into and through the cannula interior in two steps, the first step residing in pushing the implant 12 into the cannula as far as it will go and until its distal end encounters the inner end of the duct 18, and the second step residing in withdrawing the cannula 22 from the duct 18 while utilizing the thrust member 24 to prevent the implant 12 from being withdrawn with the cannula as shown in FIG. 17. In connection with withdrawal of the cannula from the duct, it is slid rearwards on the shank portion 44 of the thrust member until its rear end strikes against the end face. Such rearward sliding movement of the cannula 22 is facilitated by the provision of the out-turned ear or tab 42 (see FIG. 10) on the rear or proximal end of the cannula, such ear or tab being useable as a finger grip for such withdrawal purposes.

Figure 18:
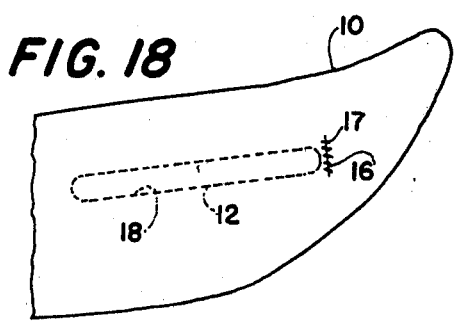
FIG. 18 is a plan view similar to FIG. 17 but showing the implant in position within the duct in the ear of the dog and the incision leading to the duct sutured.

After the cannula has been slid rearwardly over the shank portion 44 of the thrust member 24 to its fullest extent so as to remove it substantially completely from the duct 18 as shown in FIG. 17, the shank portion 44 of the thrust member 24 is withdrawn from the duct 18, leaving the implant 12 embedded within the ear as shown in FIG. 18. Withdrawal of both the cannula 22 and the thrust member 24 from the duct 18 allows the duct to collapse, so to speak, upon the implant 12, after which the initial incision 16 may be sutured as indicated by one or more stitches 17 as illustrated in FIG. 18 of the drawings.

It will be understood, of course, that after the surgical operation described above has been completed, the ear will be bandaged and otherwise treated according to acceptable medical practice and then, after a period of convalescence, practically all traces of the operation will disappear.

In FIGS. 19 and 20 of the drawings, two slightly different forms or types of cannulas are illustrated. In the former view, instead of providing an out-turned tab such as the tab 42 (see FIGS. 7 and 10) on the cannula 22, the proximate end of the cannula 122 is flared outwardly as indicated at 142, the flared portion constituting the desired finger grip. Additionally, in order to facilitate depth measurement of the duct 18 which is to be formed in the ear 10, graduations 123 in the preferred form of millimeters are shown as being applied to the body of the cannula 122. In FIG. 20, the desired finger grip is established by the provision of a rectangular extension 242 on the rear end region of the flat side wall 243 of the cannula 222, the transverse width of such extension being greater than the width of such side wall. Millimeter graduations 223 similar to the graduations 123 of the cannula 122 of FIG. 19 are likewise applied to the body of the cannula 222. In view of the similarity between the cannula 22 of FIG. 7, the cannula 122 of FIG. 19 and the cannula 222 of FIG. 20, and in order to avoid needless repetition of description, similar reference numerals but of a progressively higher order have been applied to these three views.

In FIG. 21, a slightly different form of trocar 320 is shown. Whereas the trocar 20 of FIG. 5 is provided with a shank 30 having a bevel 34 and an arcuate cutting edge 36 at its distal end, the shank 330 of the trocar 320 is formed with a pair of bevels 334 at its distal end, such bevels establishing a medial ridge 335 and a cutting point 336. Millimeter graduations 323 are provided along the shank 330 in order that the user of the trocar 320 may readily gauge the depth of the duct to be formed by said trocar.

It will be understood that, if desired, millimeter graduations similar to those shown at 123 and 323 may be applied to the cannula 22 and the trocar 20.

When performing canine ear implant operations, the above-outlined method which is schematically illustrated in FIGS. 14 through 18 has proven quite acceptable, but under certain circumstances, it may be preferable that instead of utilizing the assembled trocar and cannula combination 20, 22 for creating the duct 18 within the canine ear 10 between the cartilage and outer skin, the duct 18 be initially formed by utilizing the trocar 20 alone. After the duct 18 has thus been established, the trocar may be withdrawn, the cannula assembled thereon, and the assembly then inserted into the pre-formed duct as shown in FIG. 14. This initial creation of the duct 18 by the trocar 20 alone establishes a passage into which the trocar-mounted cannula may more readily be projected than is the case where both implements 20 and 22 are used to create the passage or duct 18.

The invention is not to be limited to the exact method steps shown in the accompanying drawings or described in this specification as various changes in the details of the method steps may be resorted to without departing from the spirit or scope of the invention. For example, although the cannula 22 is shown and described herein as being generally semi-circular in cross section, other cross-sectional shapes are contemplated. Additionally, whereas in the aforementioned surgical procedure or method, it has been stated that after the implant 12 has been lodged within the duct 18, the cannula 22 is first withdrawn and then the thrust member 24 removed, it is obvious that, if desired and if conditions permit, both of these implements may be withdrawn in unison. Therefore, only insofar as the invention is particularly pointed out in the accompanying claims is the same to be limited.

Having thus described the invention what I claim as new and desire to secure by Letters Patent is:

1. In a method of performing an implantation to correct a faulty carriage of the animal ear occasioned by the presence of a skin-enclosed cartilage fault, the improvement comprising: forcing the shank of a trocar-like implement forwardly through an incision of corresponding size in the skin of the ear, so that the shank passes between the skin and cartilage into bridging relationship with respect to the cartilage fault, providing a cannula-like sheath around said shank and between the skin and cartilage in bridging relationship with respect to the cartilage fault, then withdrawing the shank endwise and rearwardly completely from the sheath, thus leaving the sheath at least partially embedded in the ear in said bridging relationship, then inserting an elongated ear implant endwise into the thus-embedded sheath, then utilizing the shank portion of an elongated thrust member to force the inserted implant forwardly within the sheath to a region where it also bridges the cartilage fault, and then withdrawing the sheath and thrust member from the ear while leaving the implant in its bridging position.

2. The method of effecting an implantation as set forth in claim 1 and wherein the step of withdrawing the sheath and thrust member from the ear is performed by first sliding the sheath rearwards along the shank portion of the thrust member while said shank portion remains in the ear with its distal end in abutment with the adjacent end of the implant to prevent the implant from being withdrawn with the sheath, and then removing the shank portion of the thrust member with the sheath therearound completely from the ear.

3. The method of performing an implantation as set forth in claim 1 and wherein the steps of forcing said shank through the incision into bridging relationship and providing said sheath around said shank in bridging relationship are performed simultaneously by forcing an assembly of the sheath mounted on the shank through the incision.

4. The method of performing an implantation as set forth in claim 1 and wherein the steps of forcing said shank through the incision into bridging relationship and providing said sheath around said shank in bridging relationship are performed in the order named by first forcing the shank alone through the incision to form an elongated pocket-like duct between the skin and cartilage, withdrawing the shank from the thus-formed duct, and thereafter inserting an assembly of the sheath mounted on the shank through the incision and into the duct.

5. The method of effecting an implantation as set forth in claim 4 and wherein the step of withdrawing the sheath and thrust member from the ear is performed by first sliding the sheath rearwards along the shank portion of the thrust member while said shank portion remains in the ear with its distal end in abutment with the adjacent end of the implant to prevent the implant from being withdrawn with the sheath, and then removing the shank portion of the thrust member with the sheath therearound completely from the ear.

6. The method of performing a canine ear implantation to correct a faulty ear carriage occasioned by the presence of a skin-enclosed cartilage fault, said method comprising: utilizing the sharp forward cutting end of the shank of a trocar-like implement to penetrate the skin of the ear and effect an initial incision, and thereafter forcing the shank forwardly through the incision with a cannula-like sheath applied thereto so that both the shank and the sheath pass between the skin and cartilage into bridging relationship with respect to the cartilage fault, then withdrawing the shank endwise and rearwardly completely from the sheath, thus leaving the latter at least partially embedded in the ear in its bridging relationship with respect to said cartilage fault, then inserting an elongated ear implant endwise into the thus embedded sheath, then utilizing the shank portion of an elongated thrust member to force the inserted implant forwardly within the sheath to a region where it also bridges the cartilage fault, then withdrawing the sheath and thrust member from the ear while leaving the implant in its bridging position, and finally closing the incision.

7. The method of performing a canine ear implantation as set forth in claim 6 and wherein the step of withdrawing the sheath and thrust member is performed by first sliding the sheath rearwards along the shank portion of the thrust member while said shank portion remains in the ear with its distal end in abutment with the adjacent end of the implant to prevent the implant from being withdrawn with the sheath, and then removing the shank portion of the thrust member with the sheath therearound completely from the ear.

8. The method of performing a canine ear implantation to correct a faulty ear carriage occasioned by the presence of a skin-enclosed cartilage fault, said method comprising: utilizing the sharp forward cutting end of the shank of a trocar-like implement to penetrate the skin of the ear and effect an initial incision, then forcing the shank endwise and forwardly through the incision and between the cartilage and skin in order thus to form an elongated pocket-like duct which crosses over the cartilage fault, withdrawing the shank from the thus-formed duct, assembling a cannula-like sheath over the shank, then inserting the assembled shank and sheath into the duct with the sheath bridging the cartilage fault, then withdrawing the shank endwise and rearwardly completely from the sheath, thus leaving the latter at least partially embedded in the ear in its bridging relationship with respect to said cartilage fault, then inserting an elongated ear implant endwise into the thus-embedded sheath, then utilizing the shank portion of an elongated thrust member to force the inserted implant forwardly within the sheath to a region where it also bridges the cartilage fault, then withdrawing the sheath and thrust member from the ear while leaving the implant in its bridging position, and finally closing the incision.

9. The method of performing a canine ear implantation as set forth in claim 8 and wherein the step of withdrawing the sheath and thrust member is performed by first sliding the sheath rearwards along the shank portion of the thrust member while said shank portion remains in the ear with its distal end in abutment with the adjacent end of the implant to prevent the implant from being withdrawn with the sheath, and then removing the shank portion of the thrust member with the sheath therearound completely from the ear.

10. The method of performing a canine ear implantation to correct a faulty ear carriage occasioned by the presence of a skin-enclosed cartilage fault, said method comprising: first assembling an open-ended cannula-like sheath in close-fitting relationship over the shank of a trocar-like implement having a sharp forward cutting end, and utilizing the cutting end of said shank to penetrate the skin of the ear and effect an initial incision, then forcing the assembled shank and sheath endwise and forwardly between the cartilage and skin in order thus to create an elongated pocket-like duct which crosses over the cartilage fault, then withdrawing the shank endwise and rearwardly completely from the sheath, leaving the latter at least partially embedded in the duct with its rear end exposed, then inserting an elongated ear implant endwise into the exposed rear end of the sheath and causing it to slide forwardly in the sheath until it bridges the cartilage fault under the impelling force of a thrust member having a shank portion which engages the implant, then withdrawing the sheath and thrust member rearwardly and endwise completely from the duct while leaving the implant in its bridging position with respect to said cartilage fault, thus allowing the walls of the duct to shrink upon the implant for fixation purposes, and finally suturing the incision so as to retain the implant embedded in the duct with its end regions over-hanging the cartilage fault.

11. The method of performing a canine ear implantation as set forth in claim 10 and wherein said thrust member has an elongated shank portion with a blunt forward end, said shank portion being capable of sliding movement through the sheath in close fitting relationship, the step of inserting the implant is effected by projecting said shank portion endwise into the sheath so that the blunt end pushes the implant forwardly through the sheath to its fault-bridging position, and the sheath and thrust member-withdrawing step is effected by sliding the sheath rearwardly on said shank portion so that the walls of the duct, in addition to shrinking upon the implant, also shrink upon said shank portion, and thereafter withdrawing said shank portion with the sheath therearound from the duct.

* * * * *